United States Patent
Kovalcheck et al.

(10) Patent No.: US 6,572,610 B2
(45) Date of Patent: Jun. 3, 2003

(54) CRYOGENIC CATHETER WITH DEFLECTABLE TIP

(75) Inventors: Steven W. Kovalcheck, San Diego, CA (US); John Frederick Hayfield, San Diego, CA (US)

(73) Assignee: CryoGen, Inc., San Diego, CA (US)

( * ) Notice: Subject to any disclaimer, the term of this patent is extended or adjusted under 35 U.S.C. 154(b) by 0 days.

(21) Appl. No.: 09/935,296

(22) Filed: Aug. 21, 2001

(65) Prior Publication Data

US 2003/0040740 A1 Feb. 27, 2003

(51) Int. Cl.$^7$ .............................................. A61B 18/18
(52) U.S. Cl. ........................................................ 606/21
(58) Field of Search ..................... 606/20–26

(56) References Cited

U.S. PATENT DOCUMENTS

| | | | | |
|---|---|---|---|---|
| 5,395,327 A | * | 3/1995 | Lundquist et al. | 600/373 |
| 5,733,280 A | * | 3/1998 | Avitall | 606/23 |
| 6,270,476 B1 | * | 8/2001 | Santoianni et al. | 606/23 |

\* cited by examiner

*Primary Examiner*—Linda C. M. Dvorak
*Assistant Examiner*—David M. Ruddy
(74) *Attorney, Agent, or Firm*—Gerald W. Spinks (57) ABSTRACT

A flexible cryosurgical catheter having a deflectable segment adjacent its distal end, a pull wire through said catheter connected to the deflectable segment, and a deflection mechanism in its handle for pulling on the pull wire to establish a desired curvature in the deflectable segment.

8 Claims, 5 Drawing Sheets

CRYOGENIC CATHETER WITH DEFLECTABLE TIP

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention is in the field of cryosurgical catheters.

2. Background Art

In the treatment of various medical conditions, it is sometimes beneficial to apply an extremely cold temperature at one or more selected, isolated locations in or near a selected organ in the patient's body. As an example, it can be beneficial in the treatment of cardiac arrhythmia to apply cryosurgical temperatures at selected locations in the patient's heart, to create localized areas of necrotic tissue. Similarly, it can be beneficial to apply extremely cold temperatures at selected locations in other organs, or in a vascular system of the patient. The application of extremely cold temperatures can be achieved by inserting a flexible cryosurgical catheter through a vascular system to the desired location. The flexible catheter can have a heat transfer element at or near its distal end. The heat transfer element can be cooled to a cryosurgical temperature and placed in contact with a selected area of biological tissue.

It would be desirable to facilitate the application of cold temperatures by devising an apparatus with the ability to flex the tip of the cryosurgical catheter in a desired direction, to assist in guiding the catheter through a tortuous path to the selected location in or near a selected organ, or in a vascular system.

BRIEF SUMMARY OF THE INVENTION

According to certain embodiments of the invention, a surgical device is provided for applying cold temperatures at locations within the human body, via minimally invasive techniques. More specifically, the device may comprise a deflectable catheter, passable through the larger blood vessels and cavities of the heart, having a distal tip which can be deflected by remotely located means. The apparatus has conduits for the delivery and removal of refrigerant fluids within the catheter, and conductors for the monitoring of temperature and electrical impulse. A proximally located handle has a mechanism for activating the deflection of a distal catheter tip in a single plane. In certain embodiments, a flexible multiple conduit tubular vessel attached to the handle terminates in a dual channel quick connect plug for interfacing the catheter with a cryogenic fluid supply unit.

The catheter may have a torque transmitting tubular member extending from the handle to a distally located flexible tubular segment which, in turn, terminates in a high thermal conductivity tip. A deflection mechanism in the handle may manipulate the curvature of the distal flexible tubular segment of the catheter, and a braking or locking mechanism in the handle may be used to maintain a set curvature of the tip, with the tip deflection being in a predefined plane. A portion of the deflection mechanism in the handle insures that the axial tension imposed to effect deflection of the catheter tip is not transferred to the catheter shaft, thereby preventing transmission of force to the shaft. A mechanism is also incorporated into the handle to aid in the straightening of the distal tip section of the catheter, once deflection is released. A tensioning mechanism maintains a user adjustable, relatively constant tip deflection force throughout the range of motion.

Another feature that may be provided in the catheter is a device for monitoring interior catheter pressure near the catheter tip region. The conduits for refrigerant fluid delivery and removal, and the conduit for pressure monitoring are separated from the deflection mechanism in the handle, thereby relieving the need to hermetically seal the handle.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
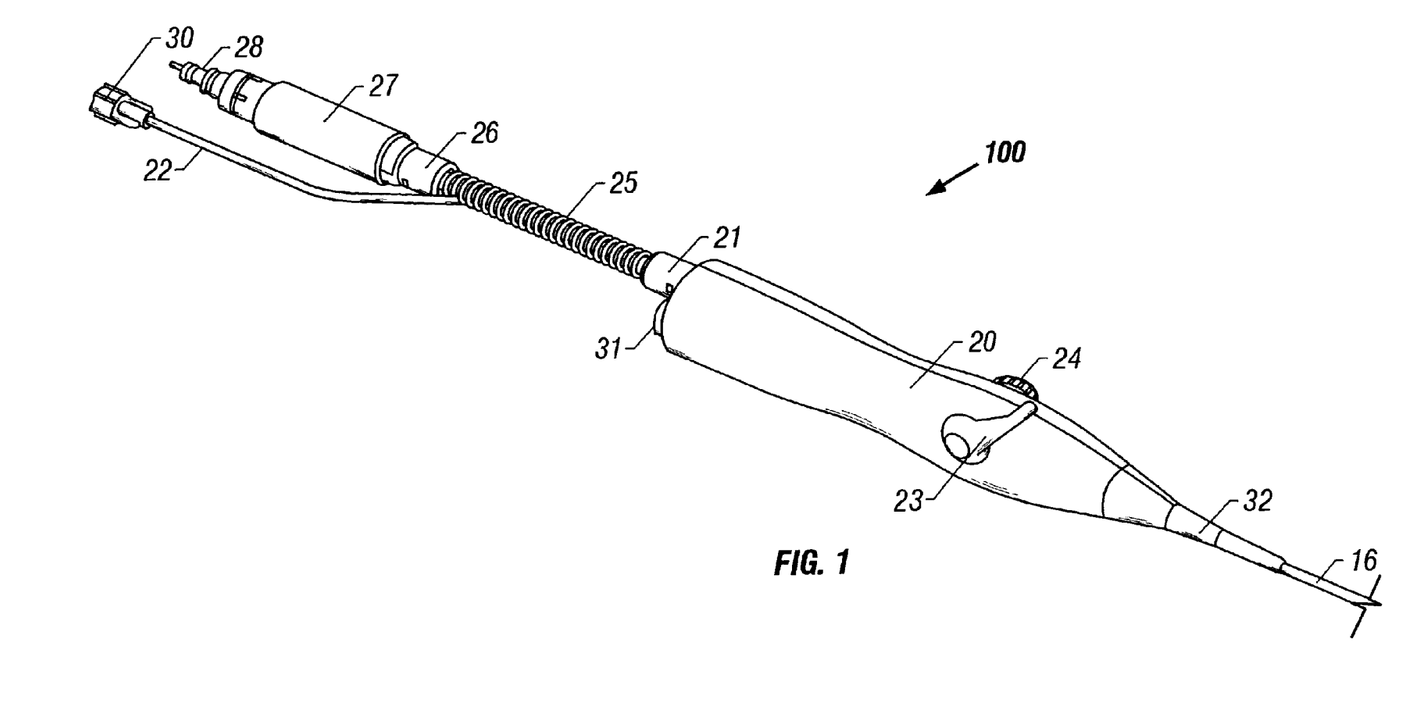
FIG. 1 is a perspective view of the apparatus according to an embodiment of the present invention.
Figure 16:
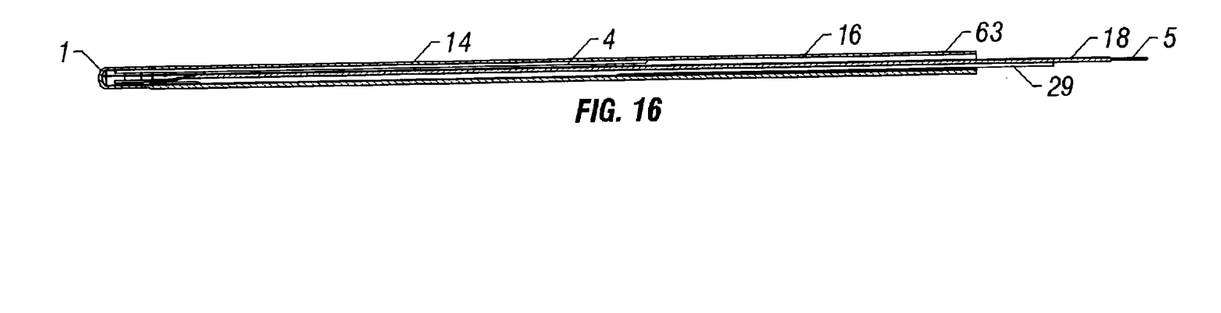
FIG. 16 is a longitudinal section view of the portion of the apparatus shown in FIG. 8.
Figure 17:
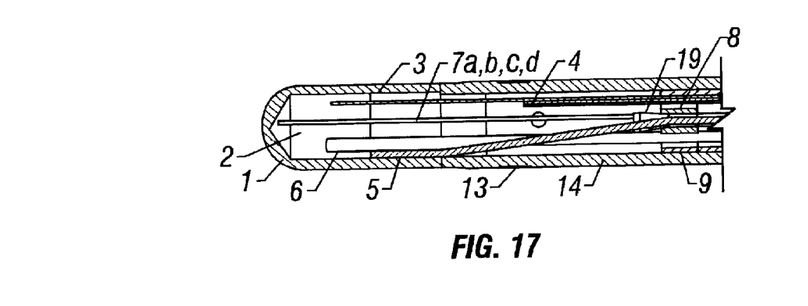
FIG. 17 is a longitudinal section view of the distal end of the portion of the apparatus shown in FIG. 16.
Figure 18:
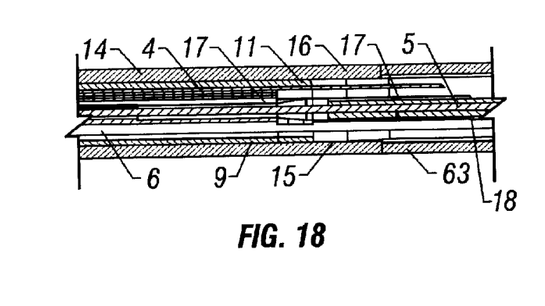
FIG. 18 is a longitudinal section view of an intermediate part of the portion of the apparatus shown in FIG. 16.

As shown in FIG. 1, the apparatus 100 includes a flexible catheter 16 attached to a handle 20, which is attached by a flexible tube 25 to a cryogenic fluid unit (not shown). As seen in FIGS. 16, 17, and 18, a spring wire 4 and a pull wire 5 are incorporated into the catheter 16, to facilitate a controlled deflection of the distal portion of the catheter 16.

As shown in FIGS. 8, 16, 17, and 18, the distal tip 1 of the catheter 16 is a closed end hollow tube which can be machined, formed, cast or molded from a highly conductive metal, preferably copper. The copper can be gold plated to insure biocompatibility. Proximal to the catheter tip 1, there can be a tip union 3 formed from a weldable metal, preferably stainless steel. The tip union 3 and the catheter tip 1 can be attached and hermetically sealed together by soldering or brazing. The tip union 3 can in turn be attached to a particularly flexible segment at the distal end of the catheter 16.

Within the chamber 2 of the catheter tip 1, a plurality of electrical conductors 7a,7b,7c,7d can be attached, for the transmission of electrical signals. The electrical conductors 7a,7b,7c,7d can be seen best in FIGS. 7 and 9 through 13. Two of the attached conductors can form a thermocouple, preferably a T type with one wire material being copper and the second being thermocouple grade constantan. A third conductor, preferably formed of nickel, can be attached to the interior of the catheter tip 1, for monitoring of electrophysiological signals. The electrical conductors can be coated with an insulating material, such as polyimide. A capillary tube 6 can terminate, at a distal end, in the chamber 2 of the catheter tip 1. The capillary tube 6 preferably has inner and outer diameters of 0.010 inches and 0.016 inches, respectively. The distal orifice of the capillary tube 6 can be located approximately 0.05 to 0.07 inches proximal to the distal end of the catheter tip 1. The capillary tube 6 is the distal extension of a high-pressure refrigerant fluid line 29 which extends proximally through the catheter 16, the handle 20, and the flexible tubular connection 25 to the cryogenic unit. The distal portion of the capillary tube 6 and its distal orifice comprise a Joule Thomson expansion element.

Welded to the interior surface of the tubular tip union 3 are two metal components, a spring wire component 4 and a pull wire component 5, both preferably stainless steel, which are located diametrically opposed to each other. The spring wire component 4 is composed of multiple flat wires, each of which is essentially rectangular in cross section, with each rectangular wire having one cross-sectional dimension significantly greater than the cross-sectional dimension perpendicular thereto. This spring wire component 4 extends proximally from the tip union 3 through, and just proximal to, the flexible segment of the catheter 16.

The flat wires are stacked and attached to each other in the spring wire component 4 to essentially form a leaf spring. More specifically, the spring wire component 4 consists of a base flat wire with a length slightly longer than the length of the distal flexible segment of the catheter 16. Near the proximal end of this base flat wire are stacked additional flat wires of progressively shorter lengths, with each having a proximal end terminating preferably a short distance distal to the proximal end of the base wire. In the preferred embodiment, there are at least three of these additional flat wires, with at least some of these having progressively shorter lengths than the base flat wire. All of the stacked flat wires preferably have similar rectangular cross-sectional dimensions.

The distal end of the base wire of the spring wire component 4 is firmly bonded or welded to the tip union 3 distal to the flexible catheter segment, and the proximal end of the base wire is firmly bonded or welded to a shaft union 15 proximal to the flexible catheter segment. The essentially rectangular leaf spring 4 functions as a spine through the flexible segment of the catheter 16, with the smaller cross-sectional dimension of the spine 4 defining a direction in which deflection of the flexible segment of the catheter 16 will occur. The spine 4 also resists deflection of the flexible catheter segment in a direction perpendicular to the defined direction of deflection.

The second metal component attached to the tip union 3 is a pull or tendon wire component 5 which, when axially tensioned, imposes a bending moment on the flexible segment of the catheter 16, with a resulting deflection in the direction defined by the spine component 4. The tendon wire 5 extends proximally from the tip union 3 to a deflection mechanism in the handle 20.

Located proximally from the catheter tip 1 is a multi-lumen core tube 9, which extends proximally, from a point approximately two catheter diameters proximal to the catheter tip 1, through the flexible segment of the catheter 16. The core tube 9 can be extruded from a polymer material having a balance between its structural properties and its elastomeric properties. A preferred material for the core tube extrusion 9 is Pebax. The core tube 9 may consist of a continuous segment, or several axially arranged segments of Pebax. For a continuous core tube 9, the hardness and the elastic modulus are constant throughout its length. For the multiple segment embodiment, each segment of core tube 9 can have a hardness and an elastic modulus less than the hardness and elastic modulus of the adjacent segment, progressing proximally to distally. This results in a core tube 9 which is softer and more flexible near its distal end than near its proximal end.

Figure 14:
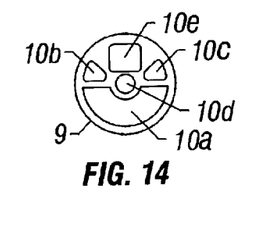

As shown in FIG. 14, the core tube 9 has multiple lumens, which can be geometrically shaped and positioned to give the flexible segment of the catheter 16 a mass moment of inertia lower in the defined direction of deflection than in the direction perpendicular to the direction of deflection. The preferred embodiment of the core tube 9 contains five lumens 10a,10b,10c,10d,10e. The core tube 9 has a central lumen 10d for passage of the tendon wire 5, and a rectangular lumen 10e positioned outwardly from the central lumen 10d. The rectangular lumen 10e is for passage of the spine wire 4. Diametrically opposite the rectangular lumen 10e, on the other side of the central lumen 10d, is located a half-annular shaped lumen 10a, through which the capillary tube 6 passes. This half-annular lumen 10a also provides a return path for low pressure refrigerant gas. Two additional lumens 10b, 10c located outwardly from the central lumen 10d carry the aforementioned electrical conductors 7a,7b, 7c,7d.

Figure 15:
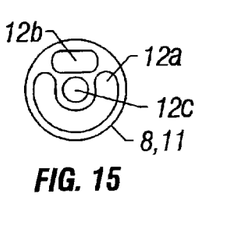

Located at the distal and proximal ends of the core tube 9 are two rigid multilumen coupler elements 8,11, preferably fabricated from a metal such as stainless steel. As shown in FIGS. 17 and 18, each coupler 8,11 is a multi-lumen tubular structure with an outer diameter equivalent in size to the outer diameter of the core tube 9. The preferred embodiment of the coupler 8,11 is a tubular structure with at least three lumens 12a, 12b, 12c, as shown in FIG. 15. These are a center circular lumen 12c, an essentially oval lumen 12b located outwardly from the center lumen 12c, and a partial annular lumen 12a that essentially encircles about ¾ of the circumference of the center lumen 12c. In the catheter assembly, the center lumen 12c of each coupler 8,11, through which the tendon wire 5 passes, axially aligns with the center lumen 10d of the core tube 9. The oval lumen 12b of each coupler 8,11, through which the spine wire 4 passes, aligns axially with the rectangular lumen 10e of the core tube 9.

The distal coupler 8 is encased in the tip union 3, and the proximal coupler 11 is encased or captured in the shaft union 15, which is also a stainless steel tube. In the preferred embodiment, the shaft union 15 is thin-walled, preferably having a wall thickness less than about 0.003 inch, and it has a length at least five times longer than the proximal coupler 11. The proximal coupler 11 is rigidly held within the shaft union 15 by mechanical means, such as a swage or bezel, or by soldering means, brazing means, welding means, or a combination of the cited means.

Figure 19:
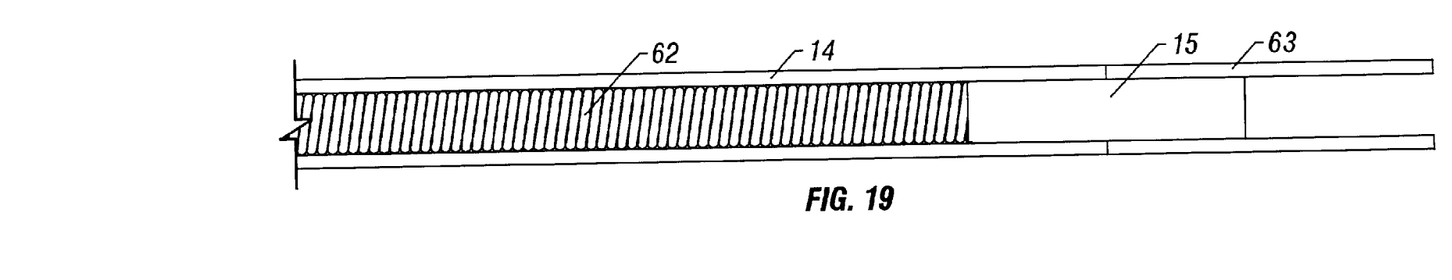
FIGS. 19 and 20 are longitudinal section views of an alternate embodiment of the distal portion of the apparatus shown in FIG. 1.
Figure 20:
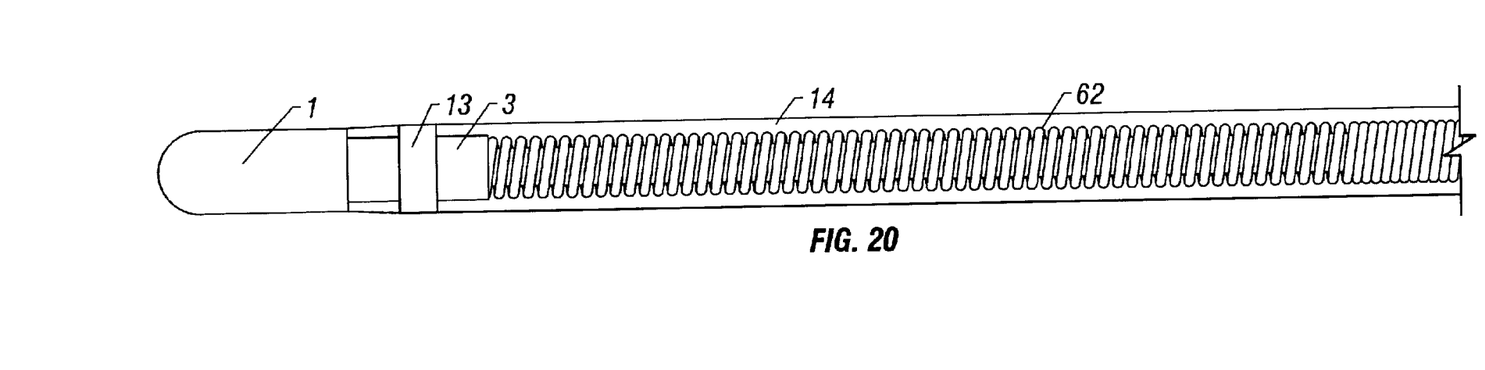
Figure 21:
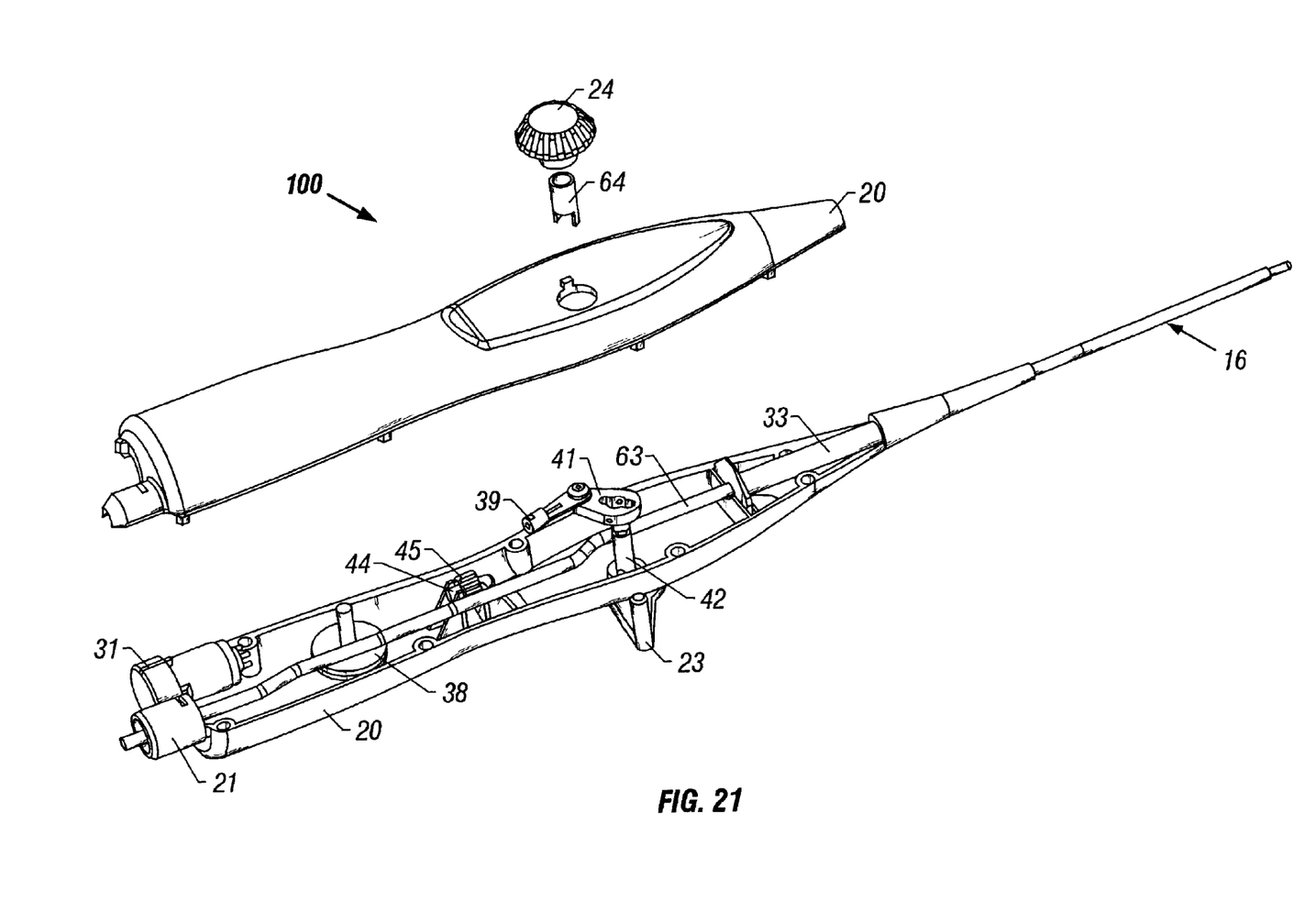
FIG. 21 is a partially exploded view of the apparatus of FIG. 1

In another embodiment shown in FIGS. 19 and 20, instead of the core tube 9, a tubular compression spring 62 extends proximally through the flexible segment of the catheter 16. The tubular spring 62 is located proximally from the tip union 3 and firmly attached thereto, by being bonded, welded, soldered, or brazed. The tubular spring 62 is composed of a flat wire having a rectangular cross section, with the smaller of the rectangular dimensions directed radially from the center of the tubular shape, and with the greater of the rectangular dimensions directed substantially axially along the tubular shape. The pitch between coils of the tubular spring 62 is designed to enable bending of the tubular spring 62 perpendicular to the axis of the catheter 16. The pitch may be fixed or variable. In the preferred embodiment, the proximal portion of the tubular spring 62 has a smaller gap between coils than the distal portion of the tubular spring 62, causing the tubular spring 62 to be more flexible near its distal end. The tubular spring embodiment also has a multi-lumen proximal coupler 11 and a shaft union 15.

Inserted into, and rigidly fixed to, the center lumen 12c of the proximal coupler 11 is a sheath union 17. The sheath union 17 is a single lumen formed metal tube. In the preferred embodiment, the sheath union 17 is firmly held to the proximal coupler 11 by mechanical means, or by being soldered, brazed or welded to the center lumen 12c of the proximal coupler 11. Inserted into, and rigidly fixed to, the center lumen 12c of the distal coupler 8 is a distal coupler union 19. The distal coupler union 19 is a single lumen formed metal tube with a flared distal end. In the preferred embodiment, the distal coupler union 19 is firmly held to the distal coupler 8 by mechanical means, or by being soldered, brazed, or welded to the center lumen 12c of the distal coupler 8.

The pull or tendon wire 5 passes from the tip union 3 through the distal coupler union 19, then through the center lumen 10d of the core tube 9 or through the spring tube 62, then into and through the sheath union 17. The essentially rectangular spine 4 passes through the oval lumens 12b of the couplers 8,11 and into the catheter shaft union 15. The spine 4 may be firmly attached to the shaft union 15 by welding means. The sensor wires 7a,7b,7c,7d passing through the core tube 9 or the spring tube 62 freely pass unobstructed through the partial annular lumens 12a of the couplers 8,11. Also passing through the partial annular lumens 12a of the couplers 8,11 is the capillary tube 6 on the distal end of the high pressure fluid line 29. The portions of the lumens 12a, 12b, 12c of the couplers 8,11 not taken up by wires and tubes make up the low pressure refrigerant gas return.

A flexible jacket 14 covers all of the catheter elements from the shaft union 15 to the tip union 3, encasing the core tube 9 or the spring tube 62, and all other internal elements. The flexible jacket 14 is a tube extruded from an elastomeric polymer with a hardness and modulus of elasticity less than or equal to the material of the core tube 9. The jacket 14 has sufficient wall thickness to maintain circularity without buckling, during the bending of the jacket 14 around a one inch radius, through a 180 degree angle. In the preferred embodiment, the jacket 14 has a length of about 5 centimeters, a diameter of about 0.130 inch and wall thickness of about 0.020 inch. The flexible tubular jacket 14 can be firmly attached to the distal portion of the outer diameter of the shaft union 15 and to the proximal portion of the outer diameter of the tip union 3, by a combination of adhesive bonding and thermal fusion. The jacket tube 14 can also be thermally fused to the core tube 9 or the spring tube 62. In the embodiment using the spring tube 62, the spring tube 62 can impart additional hoop strength to the jacket tube 14, thereby preventing buckling during bending. The adhesive bonding and thermal fusing of the jacket tube 14 to the tip union 3 and the shaft union 15 creates a hermetically sealed cavity extending from the catheter tip 1 to the shaft union 15.

Two millimeters proximal to the catheter tip 1, a sensor band 13, preferably formed from platinum, is swaged, fitted or bonded around the flexible jacket tube 14. Conductively attached to the platinum sensor band 13 is a nickel wire, which is passed through the wall of the jacket tube 14, and either into and through one of the conductor lumens 10b, 10c of the core tube 9 or between the inner diameter of the jacket tube 14 and the outer diameter of the spring tube 62, passing proximally past the shaft union 15. The sensor band 13 and the nickel wire comprise a means for sensing ECG electrical impulses.

A tightly wound wire coil sheath 18 encases the pull or tendon wire 5. The sheath 18 terminates on its distal end within the proximal portion of the sheath union 17 and is attached thereto. The sheath 18 extends proximally through the catheter 16 into the handle 20. The sheath 18 preferably has an outer diameter of about 0.021 inch, and is fabricated of tightly wound 0.003 inch diameter wire. During deflection of the tip, axial displacement and tensile force are imposed upon the pull or tendon wire 5. The sheath 18 prevents axial compression of the catheter body 16. While preventing axial compression of the catheter body 16, the coils of the sheath 18 pack together, and the sheath 18 behaves as an incompressible body, thereby allowing efficient transmission of tensile force and axial displacement to the flexible portion of the catheter 16, which results in the deflection of the flexible portion of the catheter 16.

Connected, bonded and thermally fused to the shaft union 15 and the flexible jacket tube 14 is the main catheter shaft 63. The catheter shaft 63 is a tubular element with an outer diameter comparable in size to the outer diameter of the flexible jacket 14, and with an inner diameter comparable to the outer diameter of the shaft union 15. The catheter shaft 63 is a composite structure designed to transmit torque to the catheter tip 1 and the flexible portion of the catheter 16 during manipulation of the catheter 16.

In one embodiment, the catheter shaft 63 includes a relatively stiff thin walled inner tube of thermoplastic, such as polyimide. A stainless steel wire braid is placed over the polyimide tube, and a more flexible polymer covers the wire braid. In this embodiment, the inner polyimide tube has a thickness of about 0.0015 to about 0.002 inch, the braid is woven from 0.001 inch wire, and the outer layer is a flexible polymer such as Pebax. The flexible outer layer thickness is significantly greater than the inner polyimide tube, preferably about 0.010 to about 0.015 inch. The catheter shaft 63 terminates on its distal end at the shaft union 15 and the flexible segment of the catheter 16. The catheter shaft 63 extends proximally through the handle 20, terminating proximal to the handle 20.

In another embodiment, the catheter shaft 63 is comprised of a thermoplastic extrusion with an embedded stainless steel braid. The hardness and elastic properties of the extrusion, and the pitch and number of wires in the braid are chosen to give the desired torque transfer properties to the catheter shaft 63, as is well known in the art.

The sensor conductors 7a,7b,7c,7d, the sheath-encased pull wire 5, and the capillary tube 6 exit the proximal coupler 11, enter into and pass through the catheter shaft 63, and exit the catheter shaft 63 within the interior of the handle 20. An additional small diameter tube, the gauge tube 22, is contained within the catheter shaft 63 for monitoring of the return fluid pressure. The gauge tube 22 has a preferable outer diameter of about 0.029 inches and inner diameter of about 0.024 inches. The gauge tube 22 terminates on its distal end adjacent to the proximal coupler 11 and extends proximally through the catheter shaft 63, exiting the catheter shaft 63 within the interior of the handle 20.

Figure 7:
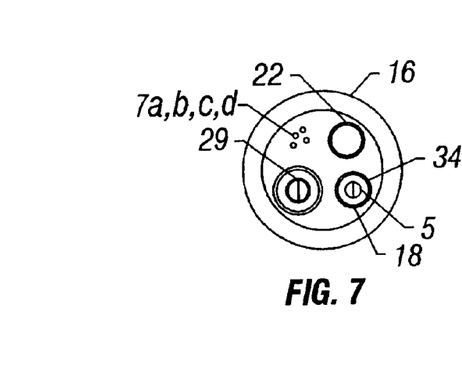
Figure 8:
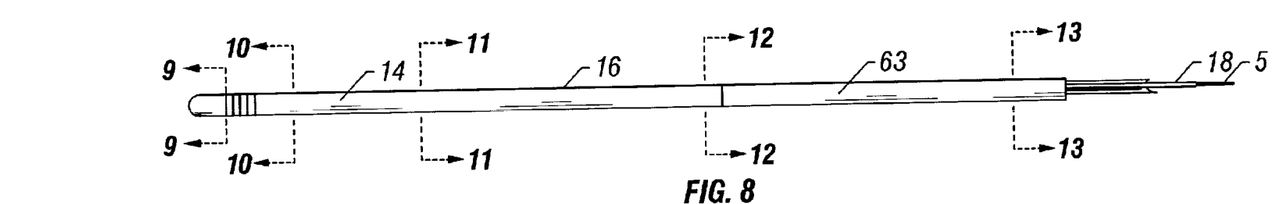
FIG. 8 is an elevation view of the distal portion of the apparatus shown in FIG. 1.
Figure 9:
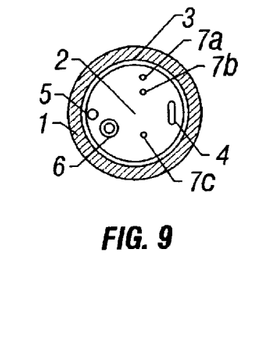
FIGS. 9 through 15 are transverse section views of the apparatus shown in FIG. 8.
Figure 10:
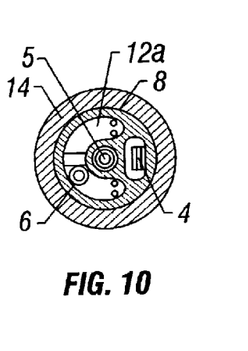
Figure 11:
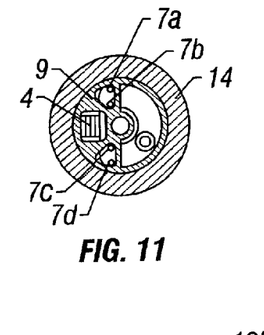
Figure 12:
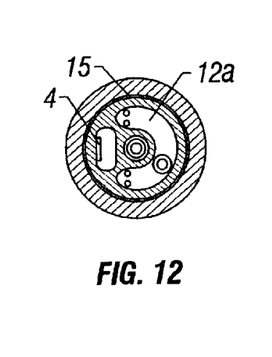
Figure 13:
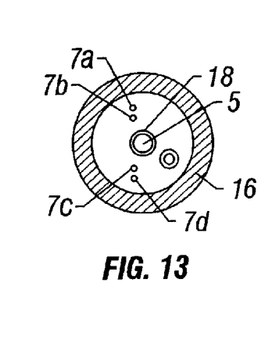

As shown in FIG. 7, a sheath tube 34 is employed about the sheath 18. The sheath tube 34 has a preferable inner diameter of about 0.024 inch, thereby allowing free movement of the sheath 18 within the sheath tube 34. During catheter usage, the pressure at the distal end of the sheath tube 34 is below atmospheric. The sheath tube 34 terminates proximally within the interior of the handle 20, where pressure is essentially atmospheric. The length and dimensions of the sheath tube 34 are designed to provide a high resistance to fluid movement between the interior of the catheter 16 and the interior of the handle 20. With the sheath 18 and the tendon 5 passing through the sheath tube 34, the available space for fluid movement between the sheath tube 34 and the sheath 18, and between the sheath 18 and the tendon 5, is minimal. Utilization of a sheath tube 34 thusly configured allows the sheath 18 and the tendon 5 components of the deflection apparatus to exit the fluid filled interior of the catheter 16 with no subsequent leakage of fluid, thereby eliminating the need to hermetically seal the handle 20.

The high pressure capillary tube 6 extends from the catheter tip 1 to a point about 10 inches proximal to the catheter tip 1, where it transitions into a larger high pressure tube 29. The transition site is hermetically sealed and can withstand pressures in excess of 1000 psi, without compromise. The high pressure tube 29 then extends proximally through the catheter shaft 63 and exits the catheter shaft 63 within the interior of the handle 20.

Figures 2, 3, 4, 5:
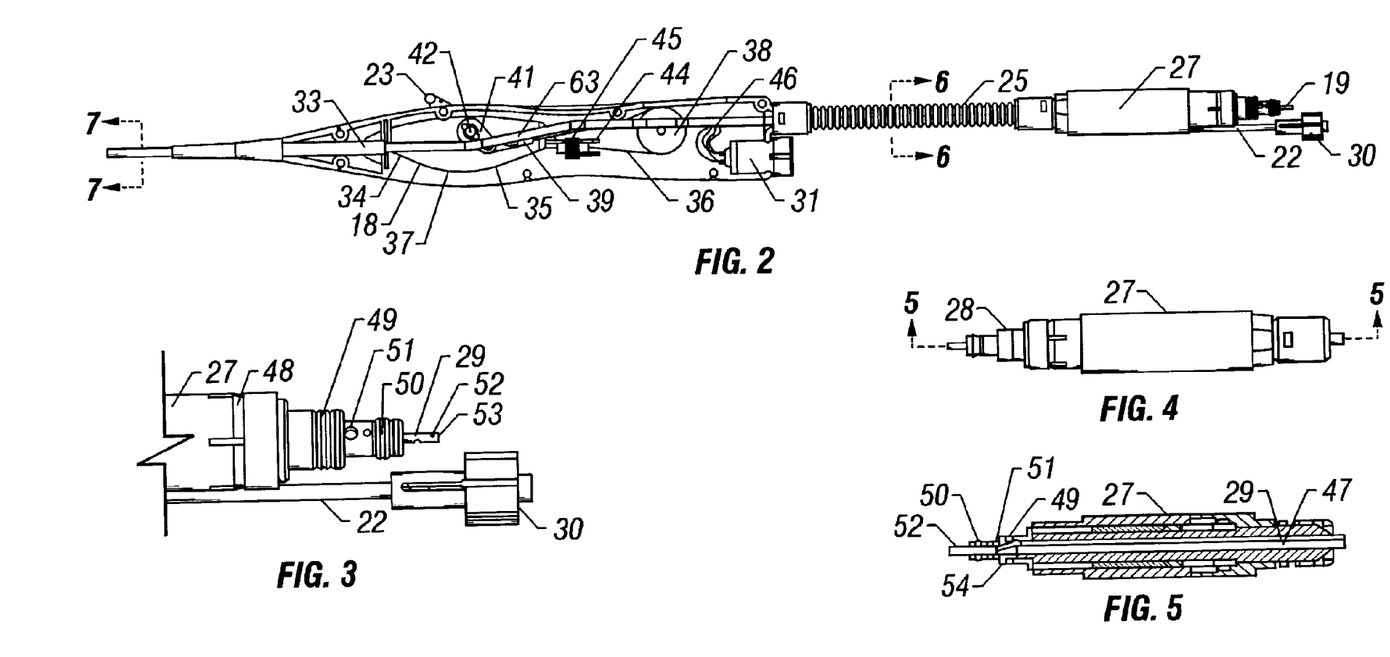
FIG. 2 is a partial longitudinal section view of the apparatus shown in FIG. 1.
FIG. 3 is an elevation view of the proximal end of the apparatus shown in FIG. 2.
FIG. 4 is an elevation view of a portion of the apparatus shown in FIG. 2.
FIG. 5 is a longitudinal section view of the portion of the apparatus shown in FIG. 4.

As shown in FIG. 2, the handle 20 incorporates a means for securing the catheter shaft 63, the articulation mechanism, an electrical connector or receptacle 3 1, and a pathway for the catheter shaft 63, the high pressure tube 29, and the gauge tube 22 to pass through. As the catheter shaft 63 enters the handle 20, it is firmly captured and bonded into the catheter support 33. The catheter support 33 is a hollow tubular structure with features on its proximal end that allow for securing to slots within the handle 20.

The catheter shaft 63 enters the handle 20 on the distal end of the handle 20, passes through the handle 20, and exits the handle 20 through an exit port on the proximal end of the handle 20. Four exit site holes are made in the wall of the catheter shaft 63 within the handle 20. The exit site holes are drilled or cut preferably at an angle of about 10 to 15 degrees off the axis of the catheter shaft 63, thereby allowing tubes within the catheter shaft lumen to exit without deformation or buckling. One exit site hole (not shown) is provided to allow the high pressure tube 29 to exit the catheter shaft 63. Another exit site hole (not shown) is provided to allow the gauge tube 22 to exit the catheter shaft 63. A third exit site hole 46 is provided to allow the sensor wires 7a,7b,7c,7d to exit the catheter shaft 63. A fourth exit site hole is provided to allow the sheath tube 34, the sheath 18 and the tendon wire 5 to exit the catheter shaft 63.

In the preferred embodiment, the high pressure tube 29 exits the catheter shaft 63 within the handle 20 at the most proximal location, extends essentially parallel to the catheter shaft 63, and exits the handle 20 through the exit port on the proximal end of the handle 20. A hermetic seal is placed about the juncture where the high pressure tube 29 exits the catheter shaft 63. Just distal to the high pressure tube exit site hole, is the gauge tube exit site hole. In the preferred embodiment, the gauge tube 22 exits the catheter shaft 63 within the handle 20, extends essentially parallel to the catheter shaft 63, and exits the handle 20 through the exit port on the proximal end of the handle 20. A hermetic seal is placed about the juncture where the gauge tube 22 exits the catheter shaft 63. At a site slightly distal to the gauge tube exit site hole, the sensor wires 7a,7b,7c,7d exit the shaft 63, pass across the handle 20 and are conductively connected, soldered, or crimped to an electrical receptacle 31. Hermetic seals are placed about the connection of the wires to the receptacle 31 and about the wire exit site hole 46 on the shaft 63.

At a site just proximal to the point where the catheter shaft 63 enters the handle 20, the sheath tube 34, the sheath 18 and the tendon wire 5 exit the catheter shaft 63. A hermetic seal is place about the sheath tube 34 exiting the catheter shaft 63. The tightly wound coil spring which makes up the sheath 18 exits the sheath tube 34, is looped slightly, and then transitions into a larger tightly wound coil spring, the sheath extension 35,36. The loop 37 in the sheath 18 as it exits the catheter shaft 63 is a service loop which allows the sheath 18 to move independently of the catheter shaft 63, thereby preventing the imposition of tensile or compressive forces on the catheter shaft 63.

The sheath extension 35,36 passes through, and is firmly bonded, welded, soldered, or brazed to an adjustment screw 44 with an attached adjustment nut 45. The adjustment screw 44 and nut 45 are securely positioned within the handle 20. Rotation of the adjustment nut 45 on the screw 44 moves the screw 44 and the attached sheath extension 35,36 distally or proximally, depending on the direction of rotation of the nut 45. Use of the adjustment screw 44 and nut 45 allows for fine adjustment of the service loop 37 of the sheath 18. The adjustment screw 44 also divides the sheath extension 35,36 into a compressive segment 35 distal to the screw 44, and a tensile segment 36 proximal to the screw 44. The purpose of this division will become apparent later.

The sheath extension 35,36 and the enclosed tendon wire 5 exit the proximal side of the adjustment screw 44 and pass around a pulley 38, to a point where they are both firmly connected, preferably swaged or crimped, to a swivel connector 39. In this connector 39, the proximal end of the tightly wound coil spring of the sheath extension 36 and the proximal end of the tendon wire 5 are joined together. The swivel connector 39 is fastened to a lever arm 41 and allowed to swivel about the connection point. The lever arm 41, an axle 42, and an activation lever 23 make up the deflection lever mechanism.

Movement of the activation lever 23 in one direction rotates the axle 42, which in turn moves the lever arm 41 to pull on the tendon wire 5 and the sheath extension 36. Movement of the lever arm 41 in this direction imparts a proximally directed displacement to both the tendon wire 5 and the proximal portion of the sheath extension 35. This proximal displacement is transmitted down the tendon wire 5 to the distal end of the distal flexible segment of the catheter 16. The initial portion of the proximal displacement works to compress the tightly wound coil of the sheath 18. The sheath 18 stiffens and prevents any further proximal displacement, and prevents compressive force from being transmitted to the catheter shaft 63, thereby allowing all remaining displacement to be used to effect a bending of the distal bendable segment of the catheter 18. During activation of tip deflection, the sheath 18 and the sheath extension 35 extending from the shaft union 15 in the catheter 16 to the adjustment screw 44 in the handle 20 are under compression. The sheath extension 36 extending from the proximal side of the adjustment screw 44 to the lever arm 41 is under tension.

Release of the activation lever 23 will cause the portion of the sheath extension 36 which is extending from the proximal side of the adjustment screw 44 to recoil and bring the lever mechanism back to its initial position. This forces the tendon wire 5 toward the catheter tip 1, and along with the assistance of the spine wire 4 and the elastic properties of the distal jacket tube 14, this results in a straightening of the distal deflection segment of the catheter 16. During activation of the deflection mechanism, the service loop 37 in the sheath 18 inside the handle 20 allows the catheter 16 to be bent without affecting tip deflection.

A locking or braking mechanism is employed on the deflection lever mechanism to allow the user to set a desired level of tension in the articulation mechanism to restrain the recoil action of the sheath extension 36, and this level of tension will then be held throughout the articulation of the tip. Also, by tightening the brake knob 24, the tension level can even be set high enough to lock the movement of the articulation mechanism to hold deflection of the distal portion of the catheter 16 in any desired position from 0 to 270 degrees. Tightening of the brake knob 24 imparts an axial force to the tension shaft 64 by means of a metal threaded insert (not shown) that is pressed into the brake knob 24. The two tabs of the tension shaft 64 in turn apply compression to drag washers (not shown). Reactive force generated by the drag washers forces the lever shaft 42 against the side of the handle 20, resisting rotation of the lever shaft 42.

Figure 6:
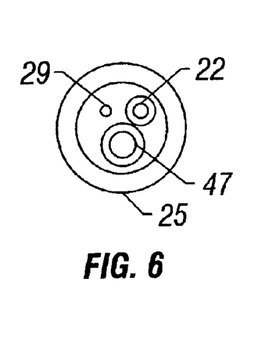
FIGS. 6 and 7 are transverse section views of the apparatus shown in FIG. 2.

Extending proximally from the handle 20 is a larger flexible tube 25, the flex line, which houses the proximal portion of the catheter shaft 63, the high pressure fluid line 29, and the gauge line 22, as shown in FIGS. 2 and 6. In the preferred embodiment, the flex line 25 is a corrugated tube constructed from a polymer such as polyethylene. The distal end of the flex line 25 is connected to the handle 20, and its proximal end is connected to a gas line connector 27. Running essentially parallel within the flex line 25 are the high pressure fluid line 29, the gauge line 22, and a continuation of the catheter shaft 63, which is the low pressure fluid line 47. The gauge line 22 exits the flex line 25 just distal to the gas line connector 27 and terminates in a standard luer fitting 30.

As shown in FIGS. 3, 4, and 5, the high pressure fluid line 29 and the low pressure fluid line 47 enter into and pass through the gas line connector 27, with the low pressure line 47 terminating at the distal portion of a dual gas line fitting 28, and with the high pressure fluid line 29 passing all the way through the dual gas line fitting 28. The tubes of the low and high pressure fluid lines 47,29 are potted to the gas line connector 27 to prevent fluid leakage. Where the low pressure fluid line 47 terminates, there are orifices 51 for the passage of fluid into a mating receptacle (not shown). Just distal to these low pressure orifices 51 is a quad o-ring 49 which prevents low pressure fluid leakage when the dual gas line fitting 28 is inserted into a mating receptacle (not shown). The high pressure fluid line 29 passes through the cavity of the gas line connector 27 and through the dual gas line fitting 28. At the proximal extremity is a check valve actuator 53 which is actually a proximal extension of the high pressure fluid line 29. High pressure orifices 52 are provided in the proximal extension of the high pressure fluid line 29, to allow for the passage of high pressure fluid into the high pressure fluid line 29. A second quad o-ring 50 is located about the dual gas line fitting 28 just distal to the high pressure orifices 52, to prevent leakage of high pressure fluid when the dual gas line fitting 28 is inserted into the mating receptacle (not shown).

The dual gas line fitting 28 has a mating and locking means 48 which allows the dual gas line fitting 28 to be securely connected to the mating receptacle (not shown).

The check valve actuator 53 located most proximally on the dual gas line fitting 28 acts to open a check valve in the precooler assembly (not shown) when the dual gas line fitting 28 is connected to the mating receptacle (not shown). Conversely, disconnecting the dual gas line fitting 28 from the mating receptacle (not shown) breaks contact between the check valve actuator 53 and the check valve (not shown), thus closing the check valve, minimizing gas escape from, or pressure change within, the cryo refrigerant system.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A cryosurgical apparatus, comprising:

a cryosurgical refrigeration unit;

a control handle connected in fluid flow communication with said refrigeration unit;

a torque transmitting flexible tubular catheter connected in fluid flow communication with said control handle, said control handle being adapted to impart axial torque to rotate said catheter;

a deflectable tubular segment at a distal end of said catheter, said deflectable segment having a higher degree of flexibility than said catheter;

a spine element within said deflectable segment, said spine element being constructed to define a preferred plane of deflection;

a heat transfer element on a distal end of said deflectable segment;

a refrigerant supply conduit within said catheter, said supply conduit being adapted to supply refrigerant from said refrigeration unit to said heat transfer element;

a tip deflection mechanism in said control handle;

a pull wire connecting said tip deflection mechanism to said heat transfer element, said tip deflection mechanism being adapted to impart tension to said pull wire to establish curvature of said deflectable segment of said catheter; and a flexible multi-lumen core tube within said deflectable segment of said catheter, said core tube being more flexible near its distal end than near its proximal end;

wherein said core tube has a plurality of longitudinal lumens configured to cause said core tube to flex more easily in a direction within said defined plane of deflection than in a direction not within said defined plane of deflection;

wherein said plurality of lumens are geometrically shaped and positioned to give said core tube a mass moment of inertia lower in said defined plane of deflection than in the direction perpendicular to said defined plane of deflection.

2. A cryosurgical apparatus, comprising:

a cryosurgical refrigeration unit;

a control handle connected in fluid flow communication with said refrigeration unit;

a torque transmitting flexible tubular catheter connected in fluid flow communication with said control handle, said control handle being adapted to impart axial torque to rotate said catheter;

a deflectable tubular segment at a distal end of said catheter, said deflectable segment having a higher degree of flexibility than said catheter;

a spine element within said deflectable segment, said spine element being constructed to define a preferred plane of deflection;

a heat transfer element on a distal end of said deflectable segment;

a refrigerant supply conduit within said catheter, said supply conduit being adapted to supply refrigerant from said refrigeration unit to said heat transfer element;

a tip deflection mechanism in said control handle;

a pull wire connecting said tip deflection mechanism to said heat transfer element, said tip deflection mechanism being adapted to impart tension to said pull wire to establish curvature of said deflectable segment of said catheter; and a flexible spring tube within said deflectable segment of said catheter, said spring tube being more flexible near its distal end than near its proximal end;

wherein said spring tube is configured to cause said spring tube to flex more easily in a direction within said defined plane of deflection than in a direction not within said defined plane of deflection;

wherein said spring tube comprises a flat wire having a rectangular cross section, with the smaller of its rectangular dimensions directed radially from the axis of said spring tube, and with the greater of its rectangular dimensions directed substantially axially along said spring tube;

wherein the pitch between coils of said spring tube is greater near the distal end of said spring tube than near its proximal end, thereby causing said spring tube to be more flexible near its distal end than near its proximal end.

3. A cryosurgical apparatus, comprising:

a cryosurgical refrigeration unit;

a control handle connected in fluid flow communication with said refrigeration unit;

a torque transmitting flexible tubular catheter connected in fluid flow communication with said control handle, said control handle being adapted to impart axial torque to rotate said catheter;

a deflectable tubular segment at a distal end of said catheter, said deflectable segment having a higher degree of flexibility than said catheter;

a spine element within said deflectable segment, said spine element being constructed to define a preferred plane of deflection;

a heat transfer element on a distal end of said deflectable segment;

a refrigerant supply conduit within said catheter, said supply conduit being adapted to supply refrigerant from said refrigeration unit to said heat transfer element;

a tip deflection mechanism in said control handle; and a pull wire connecting said tip deflection mechanism to said heat transfer element, said tip deflection mechanism being adapted to impart tension to said pull wire to establish curvature of said deflectable segment of said catheter;

wherein said deflection mechanism in said control handle comprises:

an axle pivotably mounted to said control handle;

a lever arm within said control handle, said lever arm being fixedly mounted to said axle, said lever arm being attached to said pull wire; and an activation lever mounted on said control handle, said activation lever being fixedly mounted to said axle;

wherein said activation lever is adapted to rotate said axle, which in turn is adapted to rotate said lever arm to pull on said pull wire to impart a proximally directed displacement to said pull wire, thereby establishing said curvature of said deflectable segment of said catheter.

4. A cryosurgical apparatus, comprising:

a cryosurgical refrigeration unit;

a control handle connected in fluid flow communication with said refrigeration unit;

a torque transmitting flexible tubular catheter connected in fluid flow communication with said control handle, said control handle being adapted to impart axial torque to rotate said catheter;

a deflectable tubular segment at a distal end of said catheter, said deflectable segment having a higher degree of flexibility than said catheter;

a spine element within said deflectable segment, said spine element being constructed to define a preferred plane of deflection;

a heat transfer element on a distal end of said deflectable segment;

a refrigerant supply conduit within said catheter, said supply conduit being adapted to supply refrigerant from said refrigeration unit to said heat transfer element;

a tip deflection mechanism in said control handle;

a pull wire connecting said tip deflection mechanism to said heat transfer element, said tip deflection mechanism being adapted to impart tension to said pull wire to establish curvature of said deflectable segment of said catheter; and an adjustable braking mechanism on said deflection mechanism, said braking mechanism being adapted to selectively restrain axial displacement of said pull wire during deflection of said deflectable segment of said catheter while maintaining a set tension when said deflection mechanism is moved over the range of motion.

5. A cryosurgical apparatus, comprising:

a cryosurgical refrigeration unit;

a control handle connected in fluid flow communication with said refrigeration unit;

a torque transmitting flexible tubular catheter connected in fluid flow communication with said control handle, said control handle being adapted to impart axial torque to rotate said catheter;

a deflectable tubular segment at a distal end of said catheter, said deflectable segment having a higher degree of flexibility than said catheter;

a spine element within said deflectable segment, said spine element being constructed to define a preferred plane of deflection;

a heat transfer element on a distal end of said deflectable segment;

a refrigerant supply conduit within said catheter, said supply conduit being adapted to supply refrigerant from said refrigeration unit to said heat transfer element;

a tip deflection mechanism in said control handle;

a pull wire connecting said tip deflection mechanism to said heat transfer element, said tip deflection mechanism being adapted to impart tension to said pull wire to establish curvature of said deflectable segment of said catheter; and a sensor located near said distal end of said catheter.

6. The apparatus recited in claim 5, wherein said sensor comprises a thermocouple.

7. The apparatus recited in claim 5, wherein said sensor comprises an ECG sensor.

8. The apparatus recited in claim 5, wherein said spine element comprises at least two stacked flat wires arranged to make said deflectable segment more flexible near its distal end than its proximal end.

* * * * *